(12) United States Patent
Chiodo

(10) Patent No.: US 8,774,899 B2
(45) Date of Patent: Jul. 8, 2014

(54) SPECIMEN POSITIONING SYSTEM FOR IMAGING MACHINES

(76) Inventor: Chris D. Chiodo, Warren, MI (US)

( * ) Notice: Subject to any disclaimer, the term of this patent is extended or adjusted under 35 U.S.C. 154(b) by 133 days.

(21) Appl. No.: 12/927,535

(22) Filed: Nov. 17, 2010

(65) Prior Publication Data

US 2011/0092807 A1 Apr. 21, 2011

Related U.S. Application Data

(63) Continuation of application No. 11/346,850, filed on Feb. 3, 2006, now Pat. No. 7,865,226.

(51) Int. Cl.
*A61B 5/055* (2006.01)
*A01K 1/06* (2006.01)
*A61G 13/12* (2006.01)
*A61B 6/00* (2006.01)
*A61B 6/04* (2006.01)

(52) U.S. Cl.
CPC ............ *A01K 1/0613* (2013.01); *A61B 6/0457* (2013.01); *A61B 6/0421* (2013.01); *A61B 5/0555* (2013.01); *A61B 6/0428* (2013.01); *A61G 13/1295* (2013.01); *A61B 6/04* (2013.01); *A61B 6/4417* (2013.01); *A61B 6/508* (2013.01); *A61B 2503/40* (2013.01)
USPC .......................................... 600/415; 600/424

(58) Field of Classification Search
None
See application file for complete search history.

(56) References Cited

U.S. PATENT DOCUMENTS

| | | | | |
|---|---|---|---|---|
| 5,311,868 A | * | 5/1994 | Carbini et al. | 600/417 |
| 6,711,430 B1 | * | 3/2004 | Ferris et al. | 600/417 |
| 7,414,403 B2 | * | 8/2008 | Chiodo | 324/321 |
| 7,534,067 B2 | * | 5/2009 | Chiodo | 403/350 |
| 7,865,226 B2 | * | 1/2011 | Chiodo | 600/407 |
| 2001/0053878 A1 | * | 12/2001 | Ferris et al. | 600/415 |
| 2004/0200001 A1 | * | 10/2004 | Stolze et al. | 5/601 |
| 2008/0168948 A1 | * | 7/2008 | Truitt et al. | 119/417 |
| 2008/0168951 A1 | * | 7/2008 | Starr et al. | 119/751 |
| 2009/0000567 A1 | * | 1/2009 | Hadjioannou et al. | 119/755 |
| 2009/0245474 A1 | * | 10/2009 | Chiodo | 378/208 |
| 2010/0056899 A1 | * | 3/2010 | Toddes et al. | 600/411 |
| 2010/0198047 A1 | * | 8/2010 | Zagorchev et al. | 600/411 |
| 2010/0269260 A1 | * | 10/2010 | Lanz et al. | 5/601 |
| 2011/0071388 A1 | * | 3/2011 | Yared et al. | 600/425 |
| 2011/0092807 A1 | * | 4/2011 | Chiodo | 600/421 |
| 2012/0041302 A1 | * | 2/2012 | Nilson et al. | 600/427 |

* cited by examiner

*Primary Examiner* — Long V. Le
*Assistant Examiner* — Angela M Hoffa
(74) *Attorney, Agent, or Firm* — Lawrence J. Shurupoff

(57) ABSTRACT

An animal holder is provided with a specialized coupling that is releasably mountable to a number of different imaging machines such as X-ray, CAT, MRI and PET machines. Composite images created from combining images from such different machines are particularly clear due to the predetermined alignment of the animal holder within the center of the field of view of each machine.

18 Claims, 5 Drawing Sheets

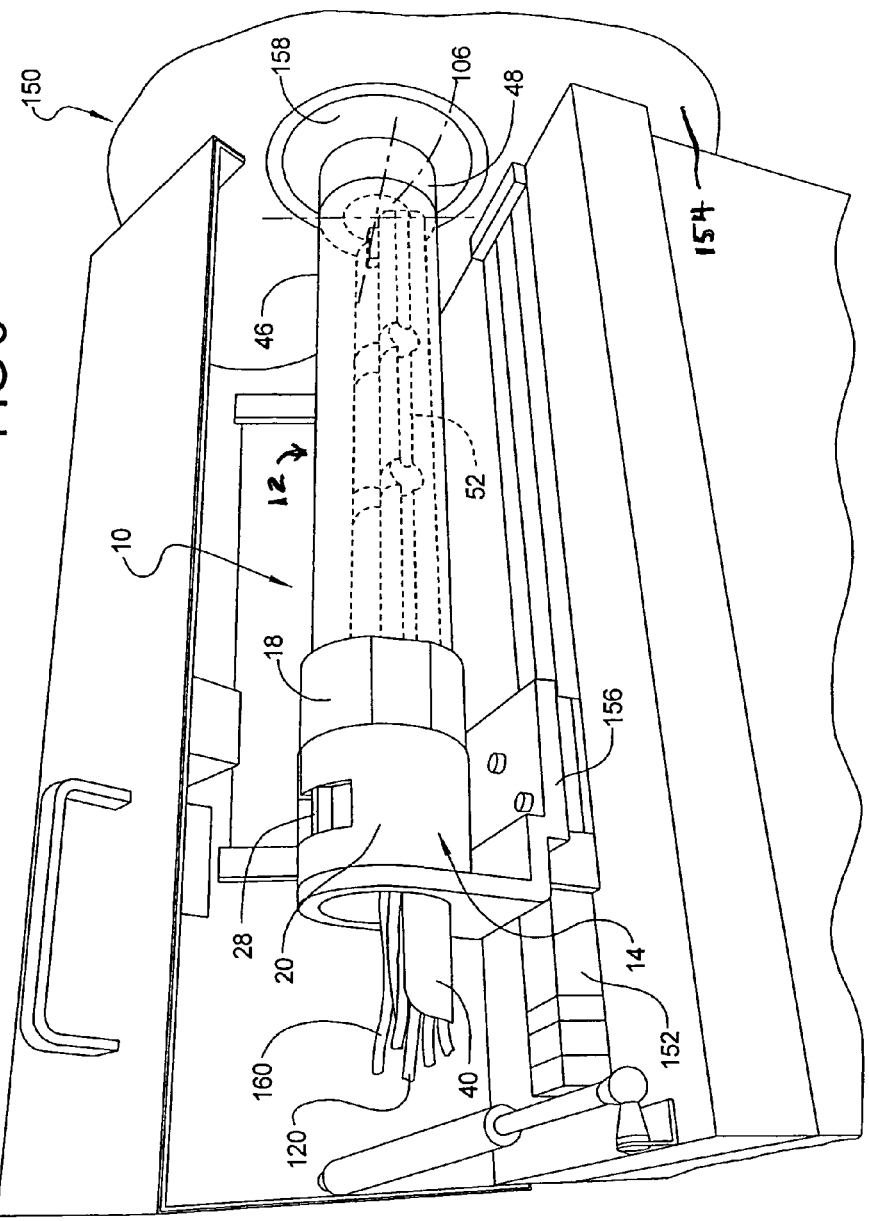

SPECIMEN POSITIONING SYSTEM FOR IMAGING MACHINES

CROSS REFERENCE TO RELATED APPLICATIONS

This application is a continuation application of U.S. application Ser. No. 11/346,850 filed on Feb. 3, 2006 now U.S. Pat. No. 7,865,226 entitled Specimen Positioning System for Imaging Machines and is incorporated herein by reference in its entirety. The benefit and priority of application Ser. No. 11/346,850 is hereby claimed.

GOVERNMENT RIGHTS

This invention was made with government support under contracts 1 R41 NS050141-01 and 3 R41 NS050141-0151 awarded by The National Institutes of Health (NIH). The government has certain rights in the invention.

BACKGROUND OF THE INVENTION

1. Field of the Invention

The present invention relates in general to apparatus for holding a specimen, such as a laboratory animal, in a fixed position during an imaging procedure such as X-ray, CAT and CT scans, MRI and PET imaging. The invention relates in particular to such apparatus which provide for the accurate repeatable positioning of a specimen time and again within the same imaging machine or within a number of different imaging machines.

2. Description of Prior Developments

In the field of medical research and patient treatment, it is often desirable to take a series of pictures or images of an anatomical feature, such as the brain, heart, knee or other organ or musculoskeletal feature over a period of time. Doctors and researchers need to review and study such features over time to understand the development, aging and changes normally associated with such features. Doctors and researchers also need to study such features as a function of the duration of a disease or pathological condition such as cancers and tumors. Doctors and researchers also need to review and monitor physiological changes in anatomical features as a function of time due to various treatments such as pharmacological and surgical treatments.

Different imaging machines are best suited for imaging different types of anatomical features. For example, bone is generally better imaged by X-ray machines and computerized axial tomography (CAT or CT) scanning machines, while soft tissue is generally better imaged by magnetic resonance imaging (MRI) machines Imaging techniques such as bioluminescent, fluorescent and photon emission tomography (PET) generally provide better bio-functional data while MRI and CT imaging generally provide better structural and anatomical data.

As a result of the strengths and weaknesses of the various imaging techniques, researchers have come to rely on the use of a combination of images from different imaging machines to produce compound or superimposed images which integrate the best features from each imaging technique. This multiple image technique requires a specimen to be imaged on and moved between a series of different imaging machines.

In order to produce accurate and clear composite images, the specimen must be accurately and repeatably positioned within each imaging machine to allow for the accurate coregistration of the various images. This has proved to be a difficult, labor intensive and time consuming setup, adjustment and alignment process.

SUMMARY OF THE INVENTION

The present invention has been developed to assist doctors and researchers in accurately and repeatably imaging the same specimen, such as a laboratory mouse or rat, over an extended period of time, such as in longitudinal time course studies, using one or more imaging machines. In accordance with the invention, a specimen may be transported in-situ from one imaging machine to the next in such a predetermined position as to facilitate the coregistration of images from one or more of the imaging machines.

That is, the present invention minimizes the variability of animal or specimen placement within the field of view of any one or more of a series of different imaging machines. This is achieved by enabling the removal of the animal or specimen from one imaging machine and the subsequent placement of the animal or specimen in the same or different imaging machine in exactly the same relative position and location time after time. This is particularly advantageous for longitudinal time course studies, where the specimen is imaged at one point in time, removed from the imaging machine and at a later time placed back into the same machine in exactly the same position and imaged again.

The present invention also minimizes the variability of animal or specimen placement when the same animal or specimen is taken from one imaging machine to the next. Images from each of a series of imaging machines may be taken of the same animal or specimen in the same position as the image taken in the first imaging machine. An animal or specimen is loaded and locked into position in accordance with the invention, and moved to each imaging device within a single common holder.

This process, apparatus and technique not only eliminates multiple setups in multiple machines, it also eliminates multiple handlings of the animal or specimen. This is particularly advantageous in those cases where the animal or specimen is contagious. Moreover, this process, apparatus and technique improves specimen position repeatability and machine setup time and throughput.

As noted above, researchers typically superimpose images from different imaging machines to form a single coregistered or composite image, taking the best features from MRI, X-ray, PET and other machines to maximize the clarity and information provided within the images. The present invention provides for the creation of clear compound images from different imaging machines by accurately positioning a specimen or patient in the same relative position in each machine. This increases the quality and reliability of coregistration of the individual images. It also increases the speed and accuracy of specialized software used to create the compound images from the different images produced by the different machines.

The present invention provides two main sections or assemblies for accomplishing the accurate and repeatable positioning of laboratory specimens such as rats and mice within the "sweet spot" or field of view of each one of various imaging machines. The first main section is a spacing or positioning receiver section and the second section is a specimen or animal holding section. A specialized coupling is provided to accurately align and connect the specimen or animal holding system to the positioning receiver assembly which can be permanently or removably mounted to an imaging machine.

In accordance with the invention, the animal holding system is releasably coupled to the positioning receiver assembly. The animal holding system is mountable interchangeably on a positioning receiver assembly on one or more imaging machines. The positioning receiver assemblies are specially adapted to mount on each respective imaging machine in such a manner that when the animal holding system is coupled to the positioning receiver assembly, the animal holding system optimally positions the animal within the field of view on each respective imaging machine.

The specialized coupling between the animal holding assembly and the positioning receiver assembly includes a male component and a female component. Each positioning receiver assembly includes the female component portion of the coupling along with a control lever to engage, lock and release the animal holding system. The animal holding system includes a male component portion of the coupling. When the male coupling portion is inserted into the female receiver coupling portion and engaged and locked, a precision, reproducible alignment coupling and connection is formed.

The combination of the positioning receiver assembly and the animal holding system produces an animal management system. From time to time an additional assembly called a positioning assembly system may be required to facilitate the placement of the animal management system into an imaging machine. This is typically required on MRI machines due to their inherent design. Each positioning assembly system, and/or as the case may be, positioning receiver assembly can be kept mounted to its respective imaging machine so that the animal holding system can be coupled to the imaging machine directly via the positioning receiver assembly or indirectly via the positioning assembly system for an MRI machine, in a highly repeatable way.

The aforementioned objects features and advantages of the invention will in part, be pointed out with particularity, and will, in part, become obvious from the following more detailed description of the invention, taken in conjunction with the accompanying drawings, which form an integral part thereof.

BRIEF DESCRIPTION OF THE DRAWINGS

In the drawings:

FIG. 5 is a perspective view of a third embodiment of the invention showing the animal management system mounted to another CT machine.

DETAILED DESCRIPTION OF THE PREFERRED EMBODIMENTS

Figure 1:
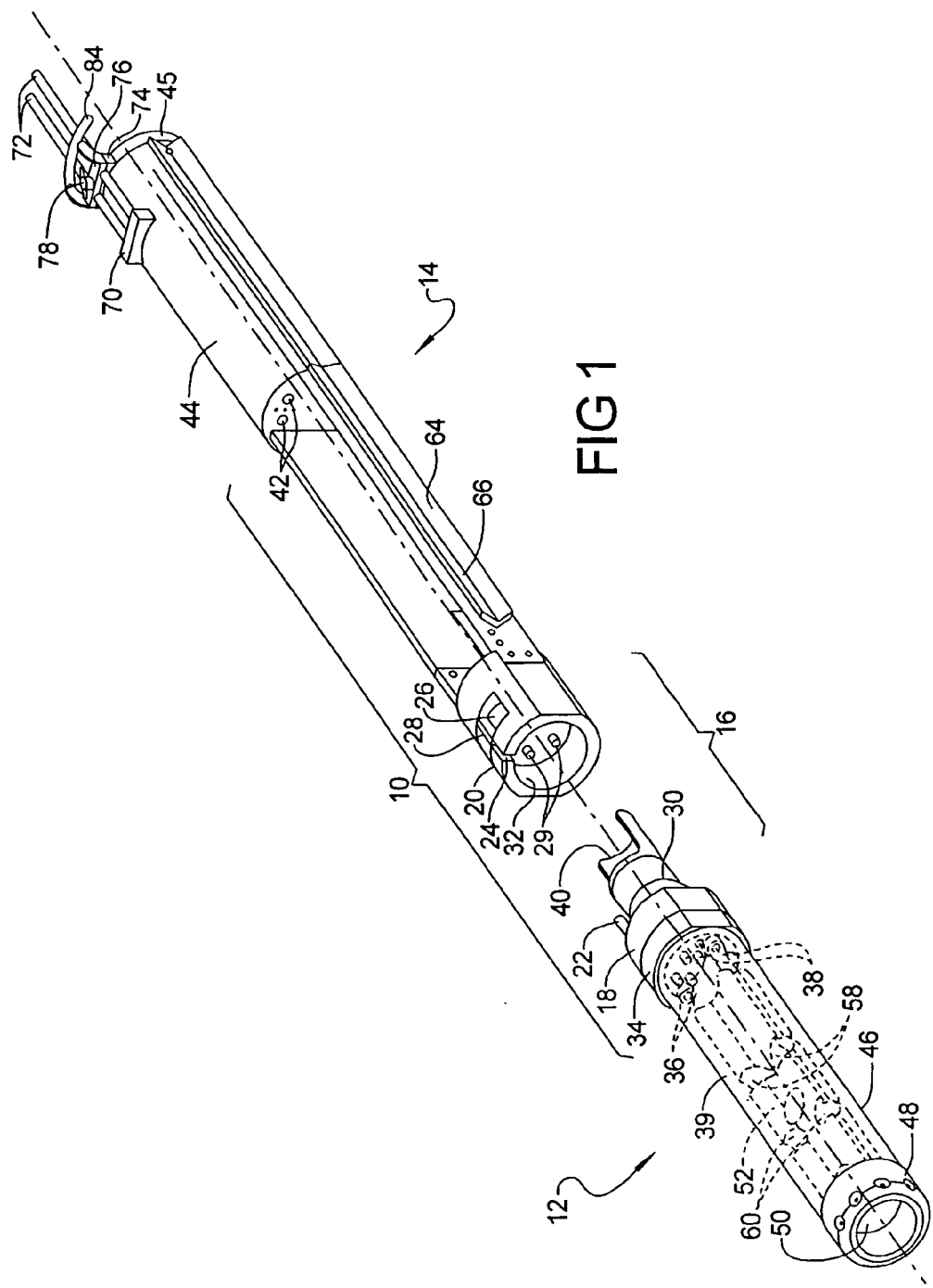
FIG. 1 is a perspective exploded view of a first embodiment of an animal management system, also called a specimen positioning system, constructed in accordance with a first embodiment of the invention and adapted for use in an MRI machine.

The present invention will now be described in conjunction with the drawings, beginning with FIG. 1 which shows an animal management system or specimen positioning system 10 constructed in accordance with a first embodiment of the invention. The positioning system 10 is adapted for use in an MRI positioning assembly such as disclosed in US patent application publication number US 2005/0027190A1, filed Aug. 10, 2001, under application Ser. No. 10/631,226, and which is incorporated herein in its entirety by reference.

While the specimen positioning assembly in US 2005/0027190 provides for a unitary specimen positioning assembly, the present invention provides for an equivalent modular multicomponent positioning system. That is, the positioning system 10 of the present invention includes a detachable modular specimen holder or animal holding system 12 which is removably and selectively mountable on a positioning receiver assembly 14 which is adapted for mounting on an imaging machine.

A modular coupling 16 is provided between the animal holding system 12 and the positioning receiver assembly 14 for accurately and repeatably coupling the animal holding system 12 to the positioning receiver assembly 14 to form a positioning system 10. Coupling 16 includes a male coupling portion 18 mounted on an outer end of the animal holding system 12 and a female coupling portion 20 mounted on an inner end of the positioning receiver assembly 14. If desired, the male and female portions 18, 20 of coupling 16 can be reversed, as long as all other compatible systems 10 are similarly adapted.

Once the male coupling portion 18 is inserted within the female coupling portion 20, a male keying member 22 projecting from a predetermined circumferential or clockwise position (such as 12 o'clock) on the male coupling portion 18 is inserted and guided into a complementary keying slot 24 formed in a predetermined circumferential or clockwise position (such as 12 o'clock) on the female coupling portion 20 so as to circumferentially align the animal holding system 12 with the positioning receiver assembly 14. This clockwise alignment ensures proper, accurate and repeatable placement of a specimen held within the animal holding system 12 within a known, generally horizontal, axial plane within the field of view of an imaging machine, as discussed further below.

Once the male coupling portion 18 is fully inserted within the female coupling portion 20, a cam ring 26 with internal circumferentially-extending cam ramps mounted within the female coupling portion 20 can be rotated by a cam lever or cam grip tab 28 to radially compress a circumferentially-spaced series of balls 29 loosely held within coupling portion 20 and thereby axially wedge and lock the male coupling portion 18 into a tight axial abutment against a radial registration surface on the female coupling portion 20. At the same time, a frustoconical male plug portion 30 on the male coupling member 18 is tightly seated and centered within a complimentary frustoconical female socket portion 32 formed within the female coupling portion 20.

This conical nesting centers the male coupling portion 18 within the female coupling portion 20 and thereby coaxially aligns the animal holding system 12 with the positioning receiver assembly 14. At the same time, the tight axial abutment between the male and female coupling portions 18, 20 accurately axially locates and registers the animal holding system 12 with respect to the positioning receiver assembly 14.

In order to release and separate the male coupling portion 18 from the female coupling portion 20, an operator need only rotate or push the cam tab 28 in an opposite direction to that of the locking direction. The animal holding system 12 can then be easily removed and placed in another positioning receiver assembly 14 in a different type of imaging machine. Additional details of the quick-connect and quick disconnect coupling 16 are provided in U.S. patent application Ser. No. 11/346,851, filed Feb. 3, 2006, titled, Coupling Assembly for Animal Management Systems, now U.S. Pat. No. 7,534,067.

As further shown in FIG. 1, the animal holding system 12 further includes an interconnection panel 34 which includes various ports 36 for the passage of fluids such as anesthesia gasses, and various electrical connectors 38 for the connection of sensor lead wires from ECG sensors and respiratory sensors, for example, located within animal holding chamber 39. The fluid ports 36 and electrical connectors 38 communicate with aligned passages formed through the male coupling portion 18 to which the panel 34 is connected.

A lead support tray or trough 40 receives and supports the electrical wires and fluid tubes exiting the outer end of the male coupling portion 18. These wires and tubes extend from within the panel 34, through channels or passages through the male coupling portion 18 and outwardly along the positioning receiver assembly 14. They then pass through conduits 42 formed through the cylindrical base 44 of the positioning receiver assembly 14. The tubes and electrical leads can then be respectively connected to external sources of fluids and to remote monitoring devices via an outer connector plate 45.

The specimen or animal chamber 39 includes a cylindrical tube 46 connected and hermetically sealed to the interconnection panel 34. Tube 46 may be made of clear or transparent plastic or glass. The inner end of tube 46 may terminate in a semihemispherical bulb in a manner similar to a common test tube. Alternatively, an end cap 48 can be threaded onto an inner threaded open end of tube 46 as shown in FIG. 1. In this case, a porous filter 50 is clamped or mounted to the inner end of tube 46 by end cap 48.

In order to accurately position and restrain a specimen, such as a laboratory rat, within the animal holding system 12, a live specimen alignment bed 52 is accurately positioned axially and circumferentially (clockwise) within tube 39. The outer end of the alignment bed 52 is accurately and removably mounted to the interconnection panel 34 by a pair of eyelets 54 (FIG. 3) which aligns with threaded bores in the interconnection panel 34. Threaded fasteners such as plastic screws can be used to fix the alignment bed 52 to the interconnection panel 34 via eyelets 54.

The alignment bed 52 is formed with a central longitudinal groove or channel 56 for accurately aligning and holding the body of an animal centrally within the tube 39. Channel 56 extends closely parallel with the central axis 57 of tube 39. Grooves or slots 58 are formed in alignment bed 52 for positioning and fixing in predetermined place the rear legs of an animal. Grooves or slots 60 are formed in alignment bed 52 for positioning and fixing in predetermined place the front legs of an animal.

A bite bar 62 is placed at the inner end of the alignment bed 52 to anchor an animal's teeth in a known axial position which corresponds to a position closely adjacent to the centerline of the field of view of each imaging machine into which the positioning system 10 is subsequently mounted. Ear bars and/or a head clamp (not shown) may also be provided to lock an animal's head in a predetermined axial location and radial orientation on the alignment bed 52.

The positioning receiver assembly 14 in FIG. 1 is specially configured to operate within a commercially available MRI machine. In this case, the positioning receiver assembly 14 is provided with a pair of diametrically-opposed axially-extending side rails 64. Each side rail 64 has a V-shaped axial groove 66 which self-aligns within a positioning assembly by sliding over a pair of complementary cylindrical rods in the manner described in US patent application publication number US 2005/0027190A1, mentioned above.

While the specimen positioning assembly of US 2005/0027190A1 relies on a fixed exterior annular end plate to abut against a mounting plate on a positioning assembly on the exterior of an MRI machine to provide proper registration and alignment of the specimen positioning assembly within the MRI machine, the specimen positioning system 10 of FIG. 1 has an axially-adjustable stop pad 70 which allows for axial adjustment of the positioning system 10 within the bore of an MRI machine.

Stop pad 70 is connected to a pair of slide rods 72 that are frictionally clamped between a lower double V-block 74 and an upper clamp bar 76. A thumb screw 78 is turned to raise and lower the clamp bar 76 to adjust the clamping force on the slide rods 72 so as to set the axial position of the stop pad 70, as desired. This allows a researcher to axially adjust and align a desired portion of an animal within the field of view of an imaging machine. A standard position for alignment of the brain of the specimen can be set at the fully extended (inward) position of the stop pad 80.

The lower double V-block 74 is fixed to the outer connector plate 45 through which fluid and electrical leads can pass, as described above. An arch-shaped carrying handle 84 is connected to the outer connector plate 45 to allow an operator to carry the entire positioning system. 10 as a unit, as desired, such as from one imaging machine to the next.

Figure 2:
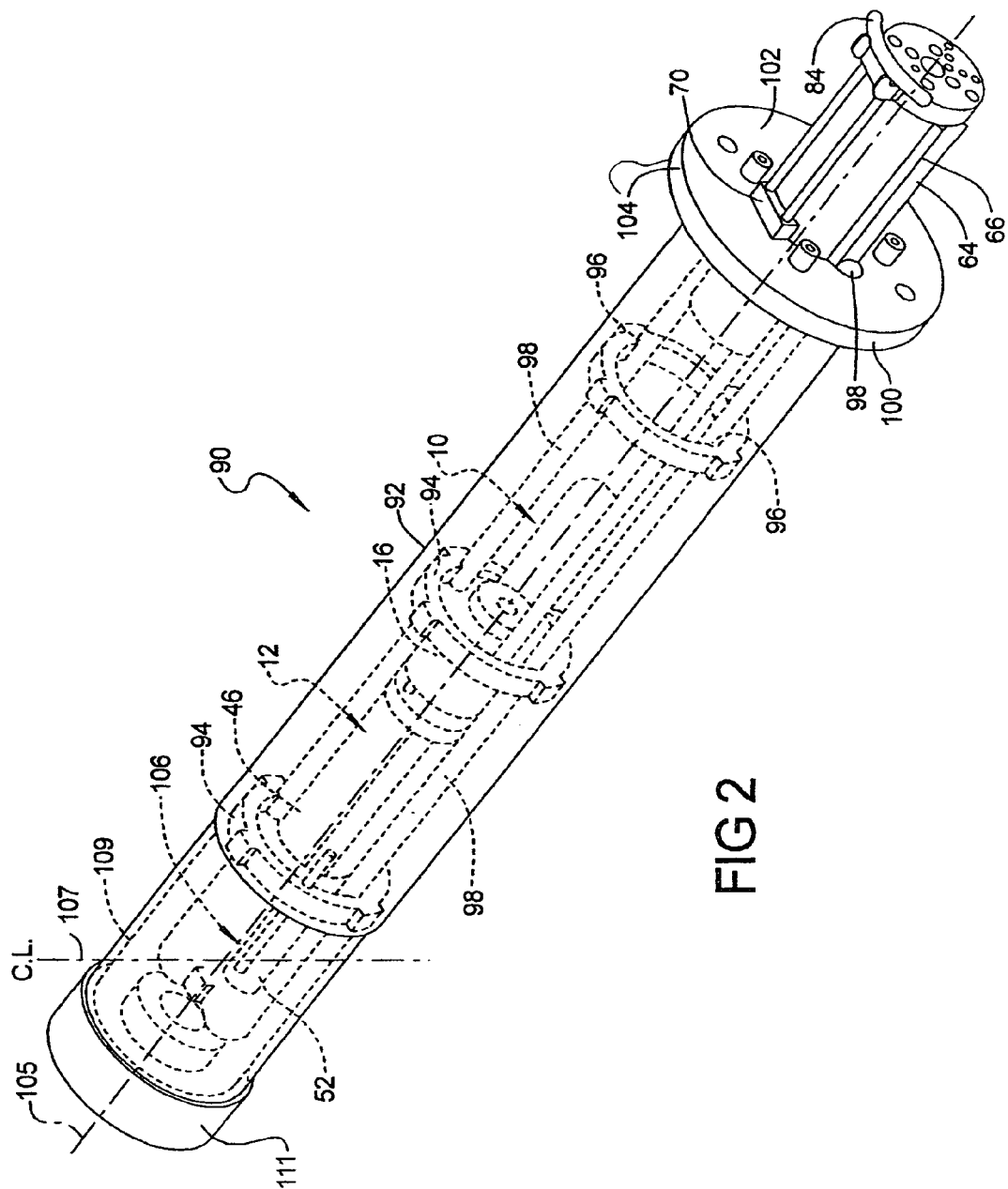
FIG. 2 is a perspective view of the animal management system of FIG. 1 mounted in a positioning assembly system adapted for mounting within the bore of an MRI machine.

The positioning system 10 of FIG. 1 is shown mounted within a mating positioning assembly system 90 in FIG. 2. The positioning assembly system 90 of FIG. 2 is adapted to be mounted within the bore of an MRI machine of conventional construction in a manner similar to that described in US 2005/0027190 A1, noted above.

The positioning assembly system 90 of FIG. 2 includes an elongated cylindrical tube 92 having a diameter closely matching that of the bore of an MRI machine within which the positioning assembly system is to be mounted. A series of axially-spaced mounting rings 94 is mounted within the tube 92 with plastic fasteners or adhesives. Each mounting ring 94 is formed with a pair of diametrically-opposed V-shaped notches 96 for accurately centering and mounting a pair of diametrically-opposed axially-aligned cylindrical guide rods 98.

Guide rods 98 are fixed to each of the mounting rings 94 and to a front mounting plate 100 with plastic fasteners, such as plastic screws. Adhesives can also be used for this purpose. The cylindrical tube 92 is also attached to the front mounting plate 100 with adhesives or plastic brackets or retainers.

As further seen in FIG. 2, the positioning system 10 of FIG. 1 is inserted into the positioning assembly system 90 by sliding the V-grooves 66 on side rails 64 over the diametrically-opposed cylindrical guide rods 98 until the stop pad 70 abuts the outer face 102 of the front mounting plate 100. In actual practice, the tube 92 of the positioning assembly system 90 will be premounted within the bore of an MRI machine, similar to a shell in a cannon bore, and the inner face 104 of the front mounting plate 100 will be tightly fixed against an exterior alignment and registration surface of the MRI machine.

The front mounting plate 100 will be fixed to the alignment and registration surface of the MRI machine in a predetermined clockwise orientation, such that the cylindrical guide rods 98 are aligned within a horizontal plane passing through the central axis 105 of the tube 92 and through the coaxially aligned bore of the MRI machine. This relationship ensures that the side rails 64 on the positioning receiver assembly 14 will be similarly aligned along with any animal holding system 12 mounted on the positioning receiver assembly 14.

The axial distance between the front face of the fully inwardly extended stop pad 70 and a predetermined imaging area 106 on the specimen alignment bed 52 is accurately dimensioned so that when the positioning system 10 is fully inserted within the positioning assembly system 90, the imaging area 106 is centrally aligned within and around the centerline or center of the field of view 107 of the imaging machine, as well as along axis 105. In this embodiment, positioning system 10 and positioning system 90 abut and register with one another to center and position the brain of a laboratory rat at the intersection of central axis 105 and centerline 107 of the imaging machine for optimal imaging of the brain.

As further seen in phantom in FIG. 2, a cylindrical tubular radio frequency coil or RF probe 109 is fixed to and between end wall 111 of tube 92 and the opposed face of the juxtaposed mounting ring 94. The axial location of coil 109 is set a predetermined axial length from the front mounting plate 100. In this manner, when the positioning system 10 is inserted within the positioning system 90, the axial location of the animal holding system 12, which is also axially set and referenced off mounting plate 100, is optimally positioned axially and coaxially within the RF probe 109. Probe 109 can be fixed to end wall 111 with plastic screws.

Once a specimen is imaged within an imaging machine fitted with the positioning assembly system 90 of FIG. 2, the positioning system 10 is withdrawn from the positioning assembly 90 and from the imaging machine by a simple axial pull on handle 84.

The positioning system 10 simply slides in and out of the positioning assembly 90, which may be permanently, semi-permanently or removably mounted to the imaging machine. Once the positioning system 10 is removed, the animal holding system 12 can be accessed and quickly released from the positioning receiver assembly 14. This is done by unlocking and releasing the coupling 16 and axially sliding the male coupling portion 18 out of the female coupling portion 20.

Figure 3:
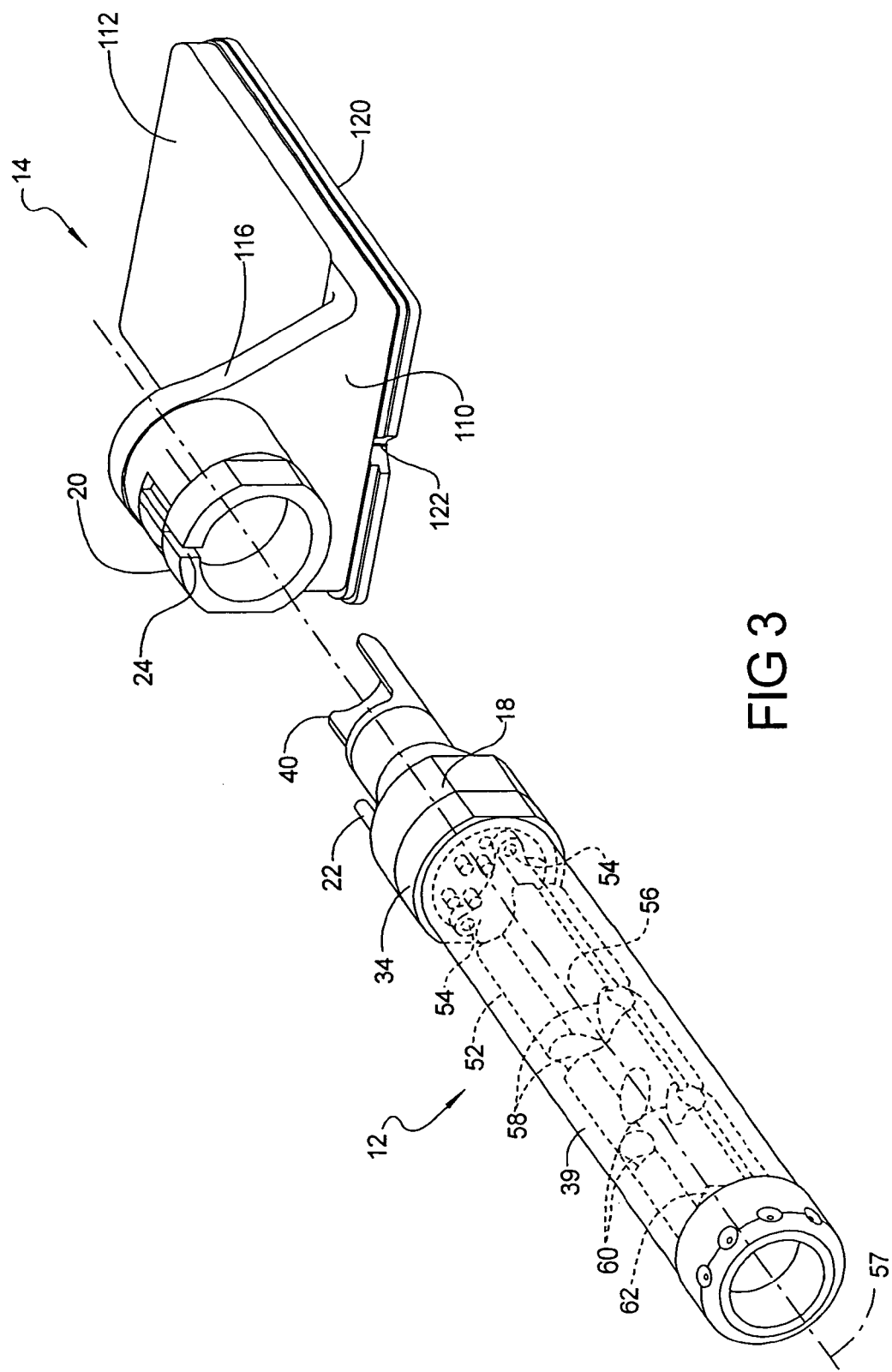
FIG. 3 is a perspective exploded view of a second embodiment of the invention showing an animal management system adapted for use in a CT or PET imaging machine.
Figure 4:
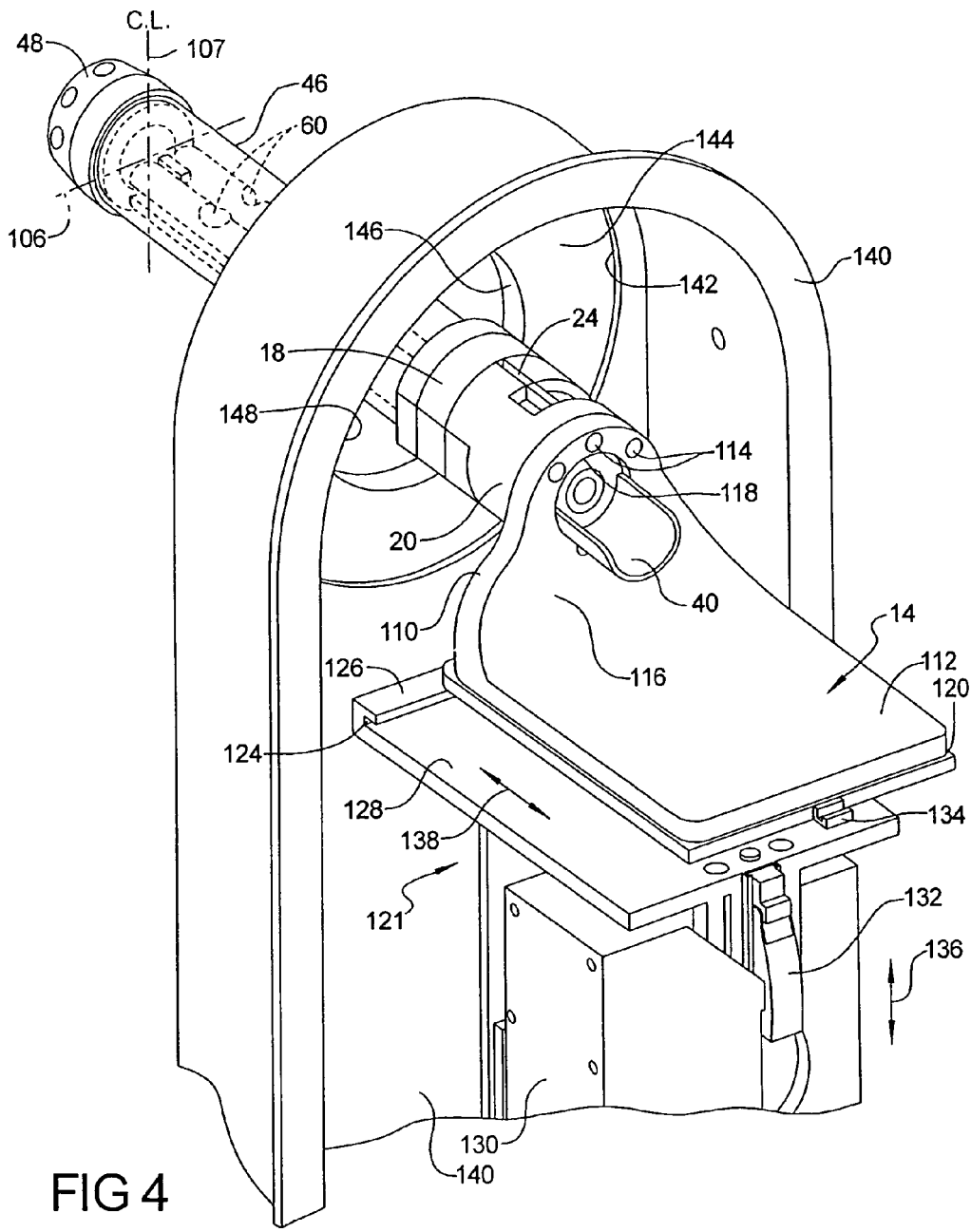
FIG. 4 is a partial perspective view of the animal management system of FIG. 3 mounted to a bracket adapted to be removably clamped or mounted on the outer face of a CT imaging machine and inserted within the bore of a CT imaging machine.

At this point, animal holding system 12 with a specimen still fixed within chamber 39 can be mounted to another positioning receiver assembly 14, such as shown in FIGS. 3, 4 and 5. In FIGS. 3 and 4, the positioning receiver assembly 14 is adapted for mounting to a micro CT and/or to a micro PET imaging machine of conventional design.

The positioning receiver assembly 14 of FIGS. 3 and 4 is in the form of a relatively simple bracket and plate configuration. A modular female coupling portion 20 is accurately and rigidly mounted in a predetermined axial and circumferential orientation to the front face of a vertical mounting bracket 110 fixed to a flat rectangular horizontal mounting plate 112.

As in the previous example, the circumferential or clockwise orientation of the female coupling portion 20 is closely and accurately fixed so that when the male keying member 22 on the male coupling portion 18 on the animal holding system 12 is inserted in the keying slot 24 in the female coupling portion 20, the animal holding system 12 will be fixed in a corresponding predetermined clockwise position with respect to the positioning receiver assembly 14. As seen in FIG. 4, the female coupling portion 20 is rigidly fixed to the mounting bracket 110 by a set of mounting screws 114.

Bracket 110 may include a mounting arch or collar 116 which surrounds a circular bore 118 (FIG. 4) formed through the upper portion of bracket 110. A lead support tray 40 extends through bore 118 for the support of fluid tubing and electrical sensor wires. In the example shown, bracket 110 is arranged substantially perpendicular to the mounting plate 112.

A mounting flange 120 is fixed to the bottom of mounting plate 112 for aligning and mounting the positioning receiver assembly 14 to an external support assembly 121 for a CT or PET machine, as shown in FIG. 4. A V-shaped notch 122 (FIG. 3) is formed in the center of the inner edge of mounting flange 120.

As seen in FIG. 4, an end block 126 is fixed to a mounting pad 128 on an actuator assembly 130 adapted for mounting on the outer surface of a CT imaging machine. The positioning receiver assembly 14, with the animal holder system 12 attached, is placed on the mounting pad 128 and pushed forwardly against end block 126. A V-shaped key (not shown) projecting outwardly from the center of end block 126 keys into the V-shaped notch 122 on mounting flange 120 and properly centers the positioning receiver assembly 14 on mounting pad 128.

At the same time, the front edge of mounting flange 120 is fully seated within a channel 124 in end block 126 to further align and position the positioning receiver assembly 14 on mounting pad 128. A clasp or over-center snap-fit type connector or latch 132 then latches over a tab or tang 134 extending outwardly from the outer edge of the mounting flange 120 to anchor and lock the positioning receiver assembly in a predetermined position. In FIG. 4, the positioning receiver assembly 14 is shown positioned just above the mounting pad 128, just prior to being anchored in position by clasp 132 and tang 134.

The actuator assembly 130 is adapted to drive the mounting pad 128 and attached positioning receiver assembly 14 up and down as shown by arrows 136 and in and out of a magnet bore as shown by arrows 138. The actuator assembly 130 can be controlled by a microcontroller or other digital indexing controller.

As further seen in FIG. 4, the actuator assembly 130 is mounted in a known predetermined orientation and position to an elongated pan-shaped bracket 140 having a large circular aperture 142 formed in its upper end portion. Bracket 140 is fixed to the front face 144 of a CT machine, such that the circular aperture 142 concentrically surrounds the circular entrance 146 to the machine bore 148 of the CT machine (not shown).

Since the dimensions and spatial locations of the machine bore 148, bracket 140, actuator assembly 130, mounting pad 128, positioning receiver assembly 14 and animal holding system 12 are mutually coordinated and predetermined, the imaging area 106 within the animal holding system 12 is preset and predetermined to coincide with the "sweet spot" or centerline 107 of the imaging machine, as in the previous example.

FIG. 5 shows yet another embodiment of the invention, wherein the specimen positioning system 10 is mounted on yet another different imaging machine, in this case a CT scanner 150. The system 10 is supported on a linear drive table 152 connected to the front surface 154 of a CT machine.

A stepped L-shaped bracket assembly 156 fixed to and supporting the positioning receiver assembly 14 mounts the animal holding system 12 to the drive table 152 for controlled linear movement into and out of the bore 158 of the imaging machine. In this example, electrical leads 160 and fluid tubing 162 are shown exiting the lead support tray 40 extending from the female coupling portion 20.

As in the prior examples, all dimensions of all components of the specimen positioning system 10 are registered, coordinated and matched with those on the respective imaging systems. In this case, they are registered with the drive table 152 and bore 158 so that the imaging area 106 will nominally be positioned within the sweet spot or centerline of the field of view within bore 158 upon controlled and coordinated actuation of drive table 152.

It can now be appreciated that the present invention provides a working system which coordinates all specimen and accompanying coil placements within the field of view of each imaging system for proper referencing. This minimizes the guesswork of where a gradient coil is positioned, where an RF probe is positioned and where/how the animal or specimen is located in relation to the centerline of the field of view of the imaging system, as all components as well as the specimen are referenced from the same relative zero point. It becomes as simple as placing the animal onto the animal holder, interfacing and connecting the animal holder with a machine specific positioning receiver assembly 14, and in the case of an MRI type imaging machine, interfacing the V-grooves and rails of the positioning assembly system 90, and sliding the animal management system 10 into the magnet bore until a mechanical stop engages a reference surface. At this point, the specimen is properly located to be imaged.

When the animal management system 10 is not utilized in an MRI type system, all these attributes are still maintained via the positioning receiver assembly 14. An operator simply loads an animal into a predetermined fixed position within the animal holder 12, and then engages the animal holder 12 with the imaging machine via a specific positioning receiver assembly 14 mounted to the imaging machine.

These characteristics of the invention form the mechanical basis that properly positions the animal within the field of view of each imaging machine. If an operator is running a series of images on different machines (modalities) with the same animal, once the animal is placed onto the animal holder 12, it is passed between and interfaced with the different machines via the machine specific positioning receivers 14, which allow for the connection of the animal holder to the machine.

For example, a research protocol could begin with an MRI scan. When the MRI scan is done, the animal management system 10 is then removed from the bore of the MRI magnet. The animal holder 12 is then disengaged from the positioning receiver assembly 14 and moved to the next imaging modality and placed in the positioning receiver assembly 14 on the next imaging machine, such as a micro CT machine. Since each imaging machine has a machine specific positioning receiver assembly already on it, the researcher merely engages the coupling 16, locks the animal holder into place via the locking lever 28, and starts the next scanning session with the specimen automatically properly positioned for optimum imaging results.

There has been disclosed heretofore the best embodiment of the invention presently contemplated. Obviously, numerous modifications and variations of the present invention are possible in light of the above teachings. It is therefore to be understood that within the scope of the appended claims, the invention may be practiced otherwise than as specifically described herein.

What is claimed is:

1. An imaging system, comprising:
    an imaging machine having an imaging bore and an imaging field of view within said imaging bore, the imaging bore having an axis;
    a positioning system comprising an animal holding assembly for holding an animal during imaging, a positioning receiver assembly for positioning said animal holding assembly at least partially in said imaging bore, a first stop surface for locating said animal holding assembly and said positioning receiver assembly in said imaging bore and a releasable coupling releasably coupling said animal holding assembly to said positioning receiver assembly;
    a positioning assembly system fixed within said imaging bore of said imaging machine in a predetermined position with respect to the field of view of the imaging machine for holding said positioning system during imaging and comprising a second stop surface; and
    said positioning system insertable within said positioning assembly system such that said positioning system is aligned in a predetermined axial position within said field of view of said imaging bore upon abutment of said first and second stop surfaces.

2. The imaging system of claim 1, wherein said first and second stop surfaces are disposed externally of said imaging bore.

3. The imaging system of claim 1, wherein said positioning assembly system comprises a pair of rods extending axially within said imaging bore and aligning said positioning system in a predetermined clockwise orientation within said imaging bore.

4. The imaging system of claim 3, wherein said animal holding assembly comprises a tube defining a hermetically sealed animal chamber.

5. The imaging system of claim 1, wherein said positioning assembly system comprises a mounting plate engaged with the imaging machine externally of said imaging bore.

6. The imaging system of claim 5, wherein said mounting plate is fixed to the imaging machine at a predetermined axial position.

7. The imaging system of claim 1, wherein said releasable coupling comprises male and female coupling portions and further comprising a second imaging machine comprising a second coupling portion releasably connectable to one of said male and female coupling portions.

8. The imaging system of claim 1, wherein said imaging machine comprises a magnetic resonance imaging machine.

9. An imaging system for imaging a laboratory specimen in different types of imaging machines, comprising:
    a first imaging machine having an imaging bore and a field of view within said imaging bore;
    a modular positioning system for releasably mounting a laboratory specimen to said first imaging machine and to a second imaging machine which produces images different from said first imaging machine, said modular positioning system comprising an animal holding assembly for holding an animal during imaging, a positioning receiver assembly for positioning said animal holding assembly in said field of view and comprising a mounting bracket, and a releasable coupling releasably coupling said animal holding assembly to said positioning receiver assembly;
    said releasable coupling comprising a male coupling portion and a female coupling portion;
    an external support assembly located in a predetermined position relative to said imaging machine and spaced apart from said imaging bore and supporting said modular positioning system and configured to move said animal holding assembly within said field of view while being entirely disposed outside said field of view;
    said mounting bracket mounted to the external support assembly in a first predetermined position and supporting said modular positioning system on said external support assembly in a second predetermined position; and one of said male and female coupling portions coupled to said animal holding assembly and the other of said male and female coupling portions coupled to said mounting bracket such that coupling of said male and female coupling portions aligns said animal holding assembly in a predetermined axial position with respect to said mounting bracket and with respect to said external support assembly for accurate alignment into said field of view and wherein release of said releasable coupling enables removal of said animal holding assembly from said modular positioning system without removal of said positioning receiver assembly from said mounting bracket.

10. An imaging system for imaging a laboratory specimen in different types of imaging machines, comprising:
- an imaging machine having an imaging bore and an imaging field of view within said imaging bore and an external support assembly spaced apart from the imaging bore and disposed externally of and registered in position relative to the imaging bore for supporting a laboratory specimen in a predetermined position relative to said imaging machine and having an actuator assembly configured to move a laboratory specimen into said imaging field of view while said external support assembly is entirely disposed outside said field of view;
- a positioning receiver assembly coupled to said external support assembly in a first predetermined position;
- an animal holding assembly having an elongated animal bed supporting an animal's body and head;
- a first coupling portion coupled to said animal holding assembly in a second predetermined position;
- a second coupling portion coupled to said positioning receiver assembly in a third predetermined position; and
- said first and second coupling portions releasably coupled to each other such that said animal holding assembly is coupled to said positioning receiver assembly in a fourth predetermined position with respect to said external support assembly and with respect to said actuator assembly externally of the imaging machine upon coupling of said first and second coupling portions.

11. The imaging system of claim 10, wherein said external support assembly comprises a mounting pad.

12. The imaging system of claim 10, wherein said external support assembly comprises a linear actuator assembly.

13. The imaging system of claim 12, wherein said linear actuator assembly comprises a linear drive table.

14. The imaging system of claim 10, further comprising a bracket assembly coupling said animal holding assembly to said external support assembly via said positioning receiver assembly.

15. The imaging system of claim 10, wherein said first imaging machine comprises one of a positron emission tomography machine and a computerized tomography scanner machine.

16. The imaging system of claim 10, further comprising an electrical connector provided on said first coupling portion.

17. The imaging system of claim 10, further comprising a fluid port formed in said first coupling portion.

18. The imaging system of claim 10, further comprising electrical wires and fluid tubes extending from said second coupling portion.

* * * * *